(12) United States Patent
Arts et al.

(10) Patent No.: US 11,199,481 B2
(45) Date of Patent: Dec. 14, 2021

(54) SAMPLE DILUTION

(71) Applicant: LAR Process Analysers AG, Berlin (DE)

(72) Inventors: Werner Arts, Berlin (DE); Olivia Arts, Berlin (DE); Martin Glittenberg, Wuppertal (DE)

(73) Assignee: LAR Process Analysers AG, Berlin (DE)

( * ) Notice: Subject to any disclaimer, the term of this patent is extended or adjusted under 35 U.S.C. 154(b) by 281 days.

(21) Appl. No.: 15/772,179

(22) PCT Filed: Oct. 31, 2016

(86) PCT No.: PCT/DE2016/100511
§ 371 (c)(1),
(2) Date: Apr. 30, 2018

(87) PCT Pub. No.: WO2017/071696
PCT Pub. Date: May 4, 2017

(65) Prior Publication Data
US 2018/0283996 A1    Oct. 4, 2018

(30) Foreign Application Priority Data

Oct. 30, 2015 (DE) .................. 10 2015 118 586.5

(51) Int. Cl.
*G01N 1/38* (2006.01)
*G01N 33/18* (2006.01)
*G01N 35/00* (2006.01)

(52) U.S. Cl.
CPC ........... *G01N 1/38* (2013.01); *G01N 33/1806* (2013.01); *G01N 33/1846* (2013.01); *G01N 35/00584* (2013.01)

(58) Field of Classification Search
CPC .. G01N 1/38; G01N 33/1806; G01N 33/1846; G01N 35/00584; G01N 2001/002; G01N 31/12; G01N 33/18
(Continued)

(56) References Cited

U.S. PATENT DOCUMENTS 4,277,438 A    7/1981  Ejzak
4,968,485 A  * 11/1990  Morita ...................... G01N 1/38
                                                        422/509
(Continued)

FOREIGN PATENT DOCUMENTS

DE    19923139    12/2000
EP    0887643     12/1996
(Continued)

*Primary Examiner* — Matthew D Krcha
*Assistant Examiner* — Jacqueline Brazin
(74) *Attorney, Agent, or Firm* — Volpe Koenig

(57) ABSTRACT

A sample analysis appliance for the analysis of a sample solution, in particular of contaminated water or of waste water, with a reaction vessel for the thermal digestion of a portioned sample of the sample solution to be analyzed. The reaction vessel has an injection port for the introduction of the sample into the reaction vessel, at least one sample solution storage vessel for the device-internal storage of sample solution, and an injection syringe device which is movable between the sample solution storage vessel and the reaction vessel and which can be controlled to collect the sample from the sample solution storage vessel and introduce the sample into the injection port of the reaction vessel. At least one first and one second sample solution storage vessel are provided, and the second sample solution storage vessel is designed for the production and storage of diluted sample solution, and the injection syringe device is designed to introduce sample solution, collected from the first sample solution storage vessel, optionally into the second sample (Continued)

solution storage vessel for producing the diluted sample solution.

14 Claims, 2 Drawing Sheets

(58) Field of Classification Search
USPC .......................................................... 436/62
See application file for complete search history.

(56) References Cited

U.S. PATENT DOCUMENTS

| | | | |
|---|---|---|---|
| 5,567,388 A * | 10/1996 | Morita | G01N 33/1846 210/321.75 |
| 6,143,568 A | 11/2000 | Pilz | |
| 6,447,725 B1 * | 9/2002 | Inoue | G01N 33/1846 422/78 |
| 6,464,999 B1 * | 10/2002 | Huo | A61F 2/0022 424/400 |
| 8,101,417 B2 | 1/2012 | Conway et al. | |
| 2004/0086425 A1 * | 5/2004 | Jaunakais | G01N 1/2273 422/86 |
| 2006/0202670 A1 * | 9/2006 | Liu | G01N 1/38 324/71.4 |
| 2010/0159602 A1 * | 6/2010 | Conway | G01N 33/1846 436/43 |
| 2013/0045540 A1 * | 2/2013 | Collier | G01N 33/1846 436/146 |

FOREIGN PATENT DOCUMENTS

| | | | |
|---|---|---|---|
| EP | 1022564 | * | 1/2000 |
| EP | 1022564 | | 7/2000 |
| EP | 2662690 | | 11/2013 |
| WO | WO-2015157698 A1 * | 10/2015 | ........... G01N 33/487 |

* cited by examiner

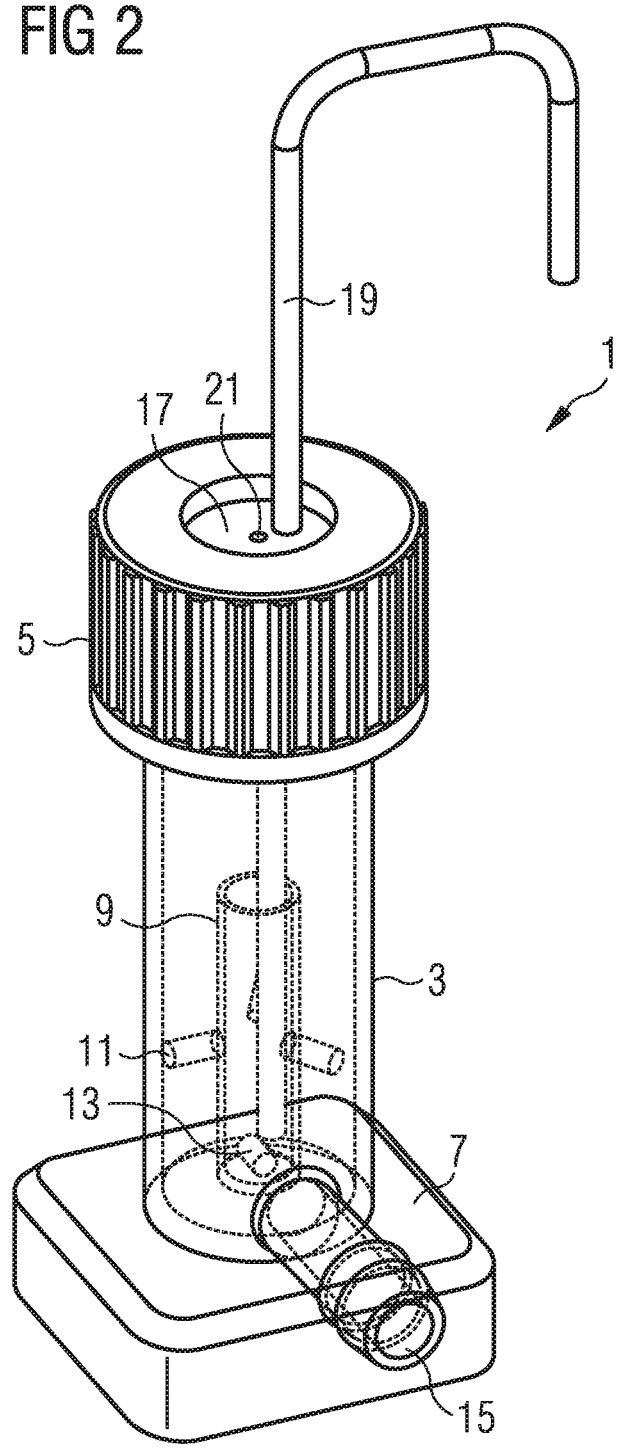

SAMPLE DILUTION

BACKGROUND

The invention relates to a sample analyzer for the analysis of a sample solution, in particular of contaminated water or of waste water, with a reaction vessel for the thermal digestion of a portioned sample of the sample solution to be analyzed, wherein the reaction vessel has an injection port for the introduction of the sample into the reaction vessel, at least one sample solution storage vessel for the device-internal storage of sample solution, and an injection syringe device which is movable between the sample solution storage vessel and the reaction vessel and which can be controlled to collect the sample from the sample solution storage vessel and introduce the sample into the injection port of the reaction vessel.

It further relates to a method of analyzing a sample solution, specifically of contaminated water or waste water, wherein the sample solution is stored device-internally and a quantitatively predetermined sample of the sample solution is thermally digested in a reaction vessel, and the digestion products are fed to a detection device for the quantitative detection of elements, in particular carbon, nitrogen or phosphorus.

It is known to burn aqueous solutions, specifically waste water or fresh water, with the intention of determining the total content of organic carbon (TOC, total organic carbon) in a reaction vessel and to feed the combustion gas to suitable detectors for detection of compounds, the detection of which allows an inference to the content of organic carbon in the aqueous solution. A method for TOC-determination is known from EP 0 887 643 A1. In this method, the sample is first raised from an initial temperature below the boiling temperature of the water to an evaporation temperature and in a second step to a significantly higher combustion temperature, preferably in the range between 800 and 1000° C. A method and apparatus for digesting an aqueous solution for determining the phosphorous content is known from DE 199 23 139 A1, in which the digestion includes a catalyst-free combustion at a temperature above 1000° C., specifically above 1200° C.

Another common parameter for quantifying the organic wastewater contamination is the total oxygen demand (TOD), the determination of which includes thermal oxidation by combustion of the sample in a high-temperature reactor. The specification JP-B-977-26111 describes a combined TOC and TOD measurement, wherein the sample is digested in a combustion chamber.

In analytical methods and corresponding apparatus of the type indicated, in addition to the primary samples (e.g. samples taken at the inlet of a wastewater treatment plant), it is often advantageous to examine diluted samples in order to obtain meaningful results. These are usually obtained by mixing a small amount of the primary sample solution with distilled water in a peripheral mixing device of the measuring arrangement and are also stored there.

SUMMARY

The object of the invention is to provide an improved sample analyzer and an improved method of the kind mentioned above by which the handling of diluted samples can be facilitated and thus the operating effort and operating costs can be reduced.

This objective is achieved in its device aspect by a sample analyzer and in its method aspect by a method with one or more features of the invention. Appropriate further developments of the inventive idea are described below and in the claims.

The invention includes the idea of embedding the provision of diluted samples directly into the analysis technique and integrating appropriate technical equipment into the actual sample analyzer. The invention includes the further idea of producing or preparing the diluted sample solution from which a diluted sample may be collected in an additional vessel of the analyzer, in which the diluted sample solution is then stored for the time period for which it is required.

Furthermore, the invention includes the idea of using the existing injection syringe device for producing the diluted sample solution, by which samples of the primary sample solution are introduced in the reaction vessel. An additional function is therefore assigned to said injection syringe device in accordance with this consideration of the inventors, eliminating the need for separate means for feeding measured quantities of the primary sample solution into the vessel to produce the diluted sample solution.

Finally, with respect to device aspects, it is intended that at least a first and a second sample solution vessel are provided, wherein the second sample solution storage vessel is designed for the production and storage of diluted sample solution, and the injection syringe device is designed to introduce/inject sample solution, collected from the first (primary) sample solution storage vessel, optionally into the second sample solution storage vessel for producing the diluted sample solution.

The invention provides a compact, clearly arranged and easily controllable analyzing arrangement by which diluted samples can be analyzed. It is obvious that such an arrangement offers space and cost advantages compared to the previously known arrangements of analyzer and peripheral equipment. The proposed method is similarly advantageous.

In one embodiment of the invention is the second sample solution storage vessel is connected to a controllable water supply for feeding distilled water to dilute the sample solution. In principle, distilled water can also be fed manually into the second sample solution storage vessel, e.g. by means of a pipette, a small water jug or the like; however, for routine analysis works such means would be in their capacity insufficient and in their handling too laborious.

According to a further embodiment, the second sample solution storage vessel has an inner vessel for the preparation and storage of the diluted sample solution, on the wall of which there is provided at least in sections an overflow area for draining away excess diluted sample solution. In this embodiment, it is possible to use the total volume of the inner vessel as a reference volume of distilled water for the preparation of the diluted sample solution. In addition, the existence of an overflow area allows for an uncomplicated rinsing of the second storage vessel between different runs of operation with different sample solutions.

In another embodiment of the invention, a stirrer for stirring the diluted sample solution is provided in the second storage vessel, in particular in the inner vessel. This allows a completely mixed diluted sample solution to be prepared in a very short time after filling the second storage vessel with water and a defined quantity of primary sample solution and to maintain its homogeneity even during a longer operating phase and operational interruptions. In a special advantageous embodiment, the stirrer is designed as a magnetic agitator with contactless drive.

In a further embodiment, to the second sample solution storage vessel, in particular to the inner vessel, a small tube for the supply of distilled water is associated, which projects into the vessel through an upper end face. The small tube is in particular connected to the water supply mentioned above or realizes it, together with a controllable valve, a pump or similar.

In a further embodiment, the first and the second sample solution storage vessel each comprise an upper end face closed with a screw cap, in which an injection port is provided for inserting an injection needle of the injection syringe device. Basically, the upper end face can also remain completely open, but in rough routine analysis mode the contents are to be protected from atmospheric contamination and therefore a cover is provided. This, in turn, could basically be formed by a septum puncturable with the injection needle, but a septum is also less suitable in routine operation with very many puncturing processes than a closure with a prefabricated opening (and at the same time a guide) for the needle of the injection syringe device. In one embodiment of the invention it is provided that that at the same time the tube assigned to the second sample solution storage vessel punctures the screw cap and is held in it.

In another embodiment, the injection syringe device can be controlled to receive different predetermined sample quantities from the first storage vessel for the preparation of diluted sample solutions of different concentrations. This is a modification of the injection syringe device of generic analyzers in that they typically collect only a single value of sample volume from the sample solution storage vessel and introduce it into the reaction vessel.

In practically relevant embodiments, the proposed sample analyzer is designed as a water or wastewater analyzer to determine the total carbon content, TC, the total inorganic carbon content, TIC, the total oxygen demand, TOD, or similar parameters. In principle, however, the application of the invention is not limited to devices for determining these parameters, nor is it necessarily limited to water and waste water analyzers, but can also be used with other analysis devices for liquid samples, wherein a dilution of the sample is required or may be desired.

As regards method aspects, the invention is characterized in that device-internally from a fed primary sample solution a diluted secondary sample solution is prepared and stored and optionally fed to the reaction vessel.

In one embodiment of the method, the diluted (secondary) sample solution is prepared by an admixture of a defined quantity of primary sample solution to a defined volume of distilled water. More specifically, the admixture is carried out in a separate sample storage vessel in such a way that it is filled with distilled water via a supply line up to a certain level of the vessel or to the overflow edge of an inner vessel provided therein and the measured quantity of primary sample solution is then injected by means of an injection syringe. However, it is understood that the implementation of the method is not limited to this practical approach.

In a further embodiment, the diluted sample solution is stirred at least temporarily, in particular permanently. The advantages of this design have already been described above under device aspects.

BRIEF DESCRIPTION OF THE DRAWINGS

Besides, further advantages and useful features of the invention will be apparent from the following description of an exemplary embodiment with reference to the Figures. These show the following:

FIG. 2 is a perspective view of a sample solution storage vessel for the absorbance of a diluted sample solution as an exemplary embodiment.

DETAILED DESCRIPTION

Figure 1:
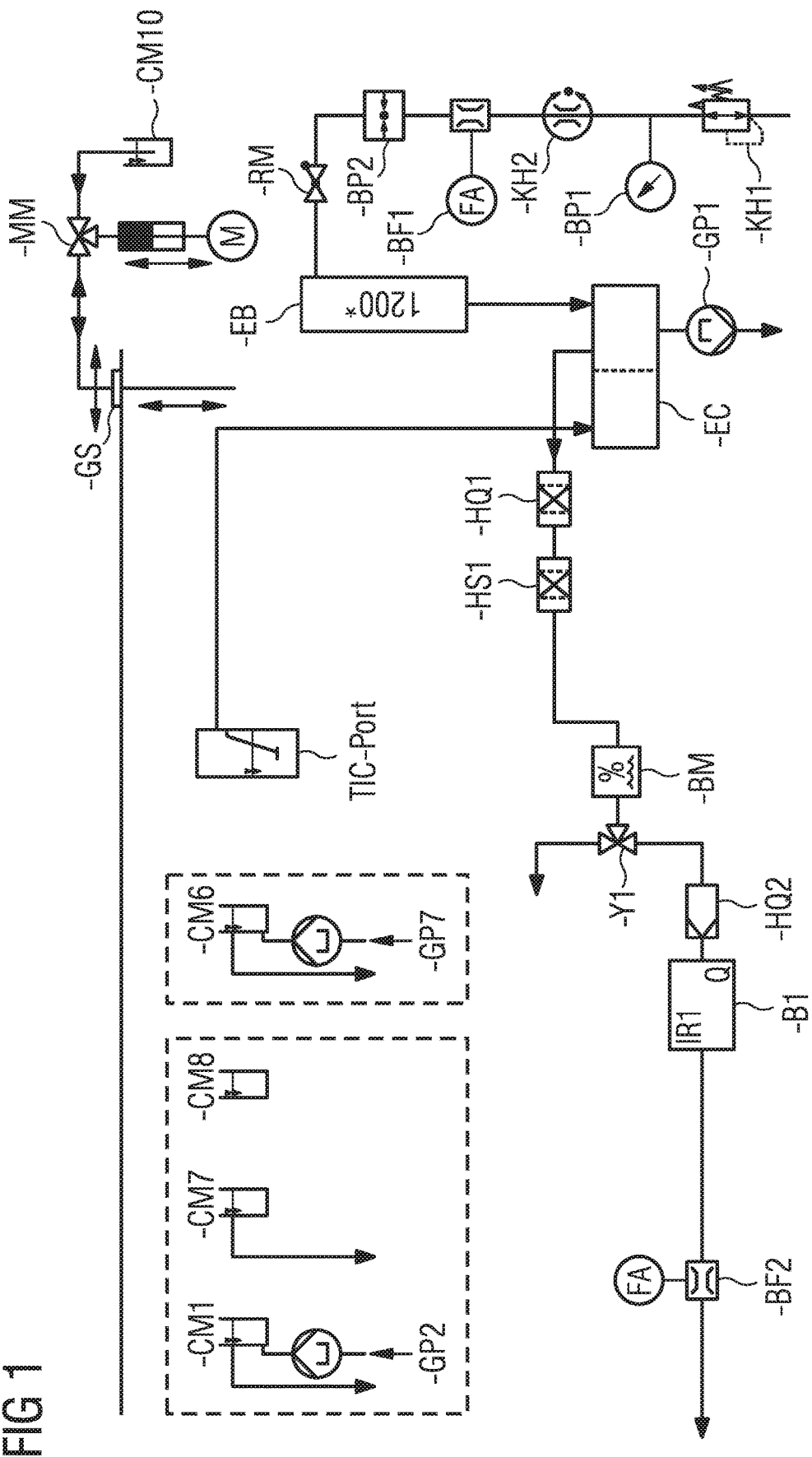
FIG. 1 is a synoptic schematic illustration of an exemplary embodiment of the sample analyzer and method according to the invention, in the form of a flow diagram.

FIG. 1 shows a schematic view of the essential components of an exemplary sample analyzer in accordance with the invention and illustrates at the same time essential aspects of the inventive method. Devices of this type—without the parts and process steps involved in sample dilution and storage and use of diluted samples—are known per se to the person skilled in the art and were previously described elsewhere, for example in the (undisclosed) German patent application 10 2014 118 138.7 of the Applicant. Therefore, the components and steps related to the invention are hereafter explained with priority.

Key components of the sample analyzer are a reaction vessel EB and a injection syringe device MM with a motor-driven and motor-actuated injection needle GS which can be moved between different vessels of the apparatus and the reaction vessel EB. A series of components is provided on the inlet of the reaction vessel, which serve to provide a properly composed and pressure and flow controlled carrier gas stream for transporting a sample digested in the reaction vessel from the reaction vessel. These are in particular a pressure reducer KH1, a pressure gauge BP1 and a flow controller KH2, a volume flow meter BF1 and a pressure sensor BP2. Directly at the inlet of the reaction vessel EB is a check valve RM provided, which serves to prevent a carrier gas backflow during injection of a sample into the reaction vessel as a result of the sudden increase in pressure.

On the outlet side of the reaction vessel EB there is a gas cooler EC and various filters, here a quartz filter HQ1, and an acid filter HS1, as well as a humidity sensor BM and a three-way valve Y1. This passes the cooled and filtered mixture of carrier gas and digested sample optionally to further device components, here to a gas filter HQ2, an IR detector B1 for $CO_2$ detection and a volume flow meter BF2. A condensate pump GP1 for draining condensate water and a TIC port on the inlet side are assigned to the gas cooler; see below.

In addition, the sample analyzer comprises a plurality of vessels for the device-internal storage of liquids required by the process. In this case, it is a first sample solution storage device (here also referred to as sample feed vessel) CM1 with an inlet in which a sample solution delivery pump GP2 is arranged, a rinsing solution storage vessel (here also referred to as "rinsing vessel") CM7 and a calibration solution storage vessel CM8. Furthermore, according to the invention, there is also a second sample solution storage vessel (here also referred to as "sample dilution vessel") CM6 with an inlet provided, wherein a delivery pump GP7 for distilled water is assigned for the preparation of the diluted sample solution prepared and stored in this storage vessel.

An exemplary procedure for preparing a diluted sample with the apparatus setup shown in FIG. 1 is as follows:

The delivery pump GP2 assigned to the first sample solution storage vessel CM1 fills the first sample solution storage device with primary (e.g. taken at the inlet of a waste water treatment plant) sample solution. When a predetermined level or overflow is reached, the delivery pump GP2 stops.

The delivery pump GP7 assigned to the second sample solution storage vessel CM6 fills this vessel (or more specifically its inner vessel; see description of an exemplary second sample solution storage vessel further below) with distilled water. When a predetermined level or overflow from the above mentioned inner vessel is detected, the delivery pump GP7 stops.

The injection syringe device MM is controlled/driven so that the injection needle GS moves to the first sample solution storage vessel (sample feed vessel) CM1, immerses into it and takes a predetermined sample volume of the primary sample solution.

Subsequently, the injection syringe device MM is controlled/driven in such a way that the needle GS moves to the second sample solution storage vessel (sample dilution vessel) CM6, immerses then in particular into the inner vessel and injects the sample volume taken from the vessel CM1 below the water level of the distilled water standing there (for example 60% lower).

Subsequently, the injection syringe device MM is actuated in such a way that the needle GS moves to the rinsing vessel CM7 to be rinsed there.

In the sample dilution vessel CM6, the sample quantity injected there and the distilled water previously filled in there is homogenized by means of a stirrer.

In a subsequent measurement of the total carbon content (TC), total nitrogen content (TN) or chemical oxygen demand (COD) of a water or wastewater sample, the following steps are performed:

The injection needle GS is moved to the sample dilution vessel CM6 where it draws up a predetermined sample volume.

Subsequently, the injection needle GS moves to the reaction vessel EB, where it introduces the sample taken from the sample dilution vessel.

The injection needle GS moves then to the rinsing vessel CM7 and is rinsed there.

The reaction product obtained in the reaction vessel EB by thermal reaction (combustion) is transported through the gas cooler EC and various filters to various detectors by means of the carrier gas supplied to the inlet side.

The detectors detect raw measured values according to their detector specifications, which are converted into analysis values of the sample by suitable software in a manner known per se.

When measuring the inorganic carbon content (TIC), where the inorganic carbon in the sample is converted into the carrier gas by acid addition in the TIC port, an exemplary process is as follows:

The injection needle GS is moved to the sample dilution vessel CM6 where it draws up a predetermined sample value.

The injection needle GS moves subsequently to the TIC port where it injects the sample drawn up from the sample dilution vessel CM6 into a specific solution, a so-called stripper. The acidic effect of the phosphoric acid contained in the stripper releases the bound $CO_2$ and directs it with the carrier gas to the $CO_2$ detector B1.

The injection syringe device MM is then actuated so that the needle GS moves to the rinsing vessel CM7 where it is rinsed.

In order to determine the organic carbon content (TOC) of a sample, suitable software is used to calculate the difference between the TC and TIC values determined in accordance with the above.

FIG. 2 shows in perspective view an embodiment of the second sample solution storage vessel (sample dilution vessel), which was referred to as CM6 in FIG. 1 and which is referred to as numeral 1 in FIG. 2. Main parts of the sample dilution vessel 1 are a cylindrical glass body (outer vessel) 3, a plastic screw cap 5 and a stirrer drive plate 7.

In the outer vessel 3, whose geometry is exemplarily matched to that of the other storage vessels mentioned above, an inner vessel 9 with a considerably smaller diameter and lower height is fixed centrically by glass spacers 11.

Near the bottom of the inner vessel 9 lies a small stirring rod 13, which is formed of magnetic material and can be rotated in a horizontally by a corresponding drive unit in the stirrer drive plate 7. Near its bottom, the dilution vessel 3 has an outlet 15.

The screw cap 5 holds a circular disc-shaped closing plate 17 of the sample dilution vessel 3, wherein an opening (not specifically marked) is provided for a small tube 17 for the supply of distilled water in the inner vessel 9 and an injection port 21 is provided for guiding the injection needle GS (FIG. 1) when injecting sample in the sample dilution vessel.

As has already been mentioned above, a diluted sample solution is prepared in a sample dilution vessel 1, wherein the inner vessel 9 is first of all filled with distilled water via the small tube 19 until it is completely filled and there is an overflow over its upper edge into the annular space to the outer vessel 3 and through the overflow 15. Then the supply of distilled water is stopped, and in a subsequent stop, the injection needle GS is moved to the sample dilution vessel 1 and inserted in the injection port 21 in such a way that its end extends deep into the inner vessel 9. In this state, the plunger of the syringe is activated and the sample volume previously collected in the sample feed vessel is injected into the inner vessel, thus preparing a diluted sample solution with a predetermined degree of dilution. This causes a quantity of distilled water equal to the sample volume to overflow and leave the outer vessel 3 through the overflow 15. Between the different measurement series with different sample dilution, the inner vessel is each time flushed with distilled water supplied via the small tube 19.

Moreover, the realization of the invention is also possible in a large number of modifications of the examples shown here and the aspects of the invention highlighted above.

The invention claimed is:

1. A sample analyzer for the analysis of a sample solution, comprising
 a reaction vessel for thermal digestion of a portioned sample of the sample solution to be analyzed, the reaction vessel has an injection port for introduction of the sample solution into the reaction vessel,
 at least one first and one second sample solution storage vessel for a device-internal storage of sample solution,
 an injection syringe device which is movable between the at least one first sample solution storage vessel which is at a first location and the reaction vessel which is at a second location, and the injection syringe device is controllable to collect the sample solution from the at least one first sample solution storage vessel and introduce the sample solution into the injection port of the reaction vessel,
 the at least one second sample solution storage vessel is adapted for the production and storage of diluted sample solution,
 the injection syringe device is further configured to be movable to a third location and to introduce the sample solution collected from the at least one first sample solution storage vessel into the at least one second sample solution storage vessel for producing the diluted sample solution, and wherein the second sample solution storage vessel has an inner vessel for the preparation and storage of the diluted sample solution, the inner vessel includes a wall on which there is at least in portions thereof an overflow area provided for draining away excess diluted sample solution.

2. The sample analyzer according to claim 1, wherein the second sample solution storage vessel is connected to a controllable water supply for feeding distilled water to dilute the sample solution.

3. The sample analyzer according to claim 1, further comprising a stirrer for stirring the diluted sample solution in the second sample solution storage vessel.

4. The sample analyzer according to claim 3, wherein the stirrer is a magnetic stirrer with contactless drive.

5. A sample analyzer for a sample solution, comprising
a reaction vessel for thermal digestion of a portioned sample of the sample solution to be analyzed, the reaction vessel has an injection port for introduction of the sample solution into the reaction vessel,
at least one first and one second sample solution storage vessel for a device-internal storage of sample solution,
an injection syringe device which is movable between the at least one first sample solution storage vessel which is at a first location and the reaction vessel which is at a second location, and the injection syringe device is controllable to collect the sample solution from the at least one first sample solution storage vessel and introduce the sample solution into the injection port of the reaction vessel,
the at least one second sample solution storage vessel is adapted for the production and storage of diluted sample solution,
the injection syringe device is further configured to be movable to a third location and to introduce sample solution collected from the at least one first sample solution storage vessel into the at least one second sample solution storage vessel for producing the diluted sample solution,
the second sample solution storage vessel is connected to a controllable water supply for feeding distilled water to dilute the sample solution, and
a tube projects into the second sample solution storage vessel through an upper end face thereof for the supply of distilled water.

6. The sample analyzer according to claim 1, wherein the first and the second sample solution storage vessels each comprise an upper end face closed with a screw cap, in which an injection port is provided for inserting an injection needle of the injection syringe device.

7. The sample analyzer according to claim 5, wherein the first and the second sample solution storage vessels each comprise an upper end face closed with a screw cap, and the tube associated to the second sample solution storage vessel punctures the screw cap and is held therein.

8. The sample analyzer according to claim 1, wherein the injection syringe device is controllable to receive different predetermined sample quantities from the first storage vessel for the preparation of diluted sample solutions of different concentrations.

9. The sample analyzer according to claim 1, wherein the sample analyzer is a water or wastewater analyzer that determines at least one of a total carbon content, a total inorganic carbon content, or a total oxygen demand.

10. A method of handling a sample solution, the method comprising: storing the sample solution in at least one first sample solution storage vessel using an injection syringe device which is movable between the at least one first sample solution storage vessel and a reaction vessel that is controllable to collect the sample solution from the at least one first sample solution storage vessel and introduce the sample solution into an injection port of a reaction vessel, thermally digesting a quantitatively predetermined sample of the sample solution in the reaction vessel, feeding digestion products to a detection device for quantitative detection of elements, and preparing and storing a diluted secondary sample solution from a fed primary sample solution for feeding to the reaction vessel using at least one second sample solution storage vessel for preparing and storage of the diluted secondary sample solution, by the injection syringe device moving to and introducing the sample solution collected from the at least one first sample solution storage vessel into the at least one second sample solution storage vessel.

11. The method according to claim 10, wherein the diluted secondary sample solution is prepared by mixing a defined quantity of the primary sample solution to a defined volume of distilled water.

12. The method according to claim 11, wherein the mixing is carried out in a separate sample storage vessel that is filled with distilled water via a supply line up to a certain level of the vessel or to an overflow edge of an inner vessel provided therein and the measured quantity of the primary sample solution is then injected by an injection syringe.

13. The method according to claim 10, further comprising stirring the diluted sample solution at least temporarily.

14. The method according to claim 10, further comprising determining at least one of a Total Carbon Content, a Total Content of Inorganic Carbon, or a Total Oxygen Demand.

* * * * *